(12) United States Patent
Grierson et al.

(10) Patent No.: US 6,204,437 B1
(45) Date of Patent: Mar. 20, 2001

(54) DNA CONSTRUCTS AND PLANTS INCORPORATING THEM

(75) Inventors: Donald Grierson, Loughborough (GB); Beatrix Blume, Halle (DE); Andrew Hamilton, Norwich (GB); Michael Holdsworth, Bristol (GB); Cornelius Barry, Loughborough (GB)

(73) Assignee: Zeneca Limited, London (GB)

( * ) Notice: Subject to any disclaimer, the term of this patent is extended or adjusted under 35 U.S.C. 154(b) by 0 days.

(21) Appl. No.: 08/894,324

(22) PCT Filed: Mar. 11, 1996

(86) PCT No.: PCT/GB96/00564

§ 371 Date: Aug. 14, 1997

§ 102(e) Date: Aug. 14, 1997

(87) PCT Pub. No.: WO96/30493

PCT Pub. Date: Oct. 3, 1996

(30) Foreign Application Priority Data

Mar. 17, 1995 (GB) .................................................. 9505608

(51) Int. Cl.⁷ .............................. A01H 5/00; A01H 1/06; C12N 15/09; C12N 15/11
(52) U.S. Cl. ..................... 800/317.4; 536/24.1; 800/298; 800/317; 800/278; 800/283; 800/287; 435/172.3; 435/320.1
(58) Field of Search ........................ 536/24.1; 435/172.3, 435/320.1; 800/205, DIG. 44, 298, 278, 283, 317, 317.4, 287

(56) References Cited

U.S. PATENT DOCUMENTS 5,365,015  *  11/1994  Grierson et al. ..................... 800/205

OTHER PUBLICATIONS

Kim et al. A 20 nucleotide upstream element is essential for the nopaline synthase (nos) promoter activity. Plant Molecular Biology. 24:105–127, 1994.*

Kock et al. eth1, a gene involved in ethylene synthesis in tomato. Plant Molecular Biology. 17:141–142. 1991.*

Holdsworth et al. Nucleotide sequence of an ethylene–related gene from tomato. Nucleic Acids Research. 15(24):10600, Dec. 1987.*

Barry et al. Differential expression of the 1–aminocyclopropane–1–carboxylate oxidase gene family of tomato. The Plant Journal. 9(4):525–535, 1996.*

* cited by examiner

Primary Examiner—Lynette R. F. Smith
Assistant Examiner—Melissa L. Kimball
(74) Attorney, Agent, or Firm—Liza D. Hohenschutz

(57) ABSTRACT

Expression of genes inserted into plants by transformation is controlled by the use of a promoter selected from Aco1, Aco2 and Aco3, the sequences of which are given. The level of expression obtained by use of these promoters varies with the stage of development of the plant.

8 Claims, 3 Drawing Sheets

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
      (A) LENGTH: 1925 base pairs
      (B) TYPE: nucleic acid
      (C) STRANDEDNESS: single
      (D) TOPOLOGY: linear (ii) MOLECULE TYPE: DNA (genomic)

(vi) ORIGINAL SOURCE:
      (A) ORGANISM: ACO1 PROMOTER (xi) SEQUENCE DESCRIPTION: SEQ ID NO: 1:

```
AGTGCTGATT ACAACATTGA AATTCTAAAT TTAGAATTTA ATATTTATTA AATGTTAGTG      60

CATTTATACA AATAACATAT TACATCTCAA ATAATATTGA GTTTGTTAGA TTTTATTTGC     120

CCTGATTTCT TATCATAAAT AGGTTTTCCT TTTAGGAAAA GGTTTTGAAT TGACTATTCT     180

TTTTTTGGTA GGAAAAAGTT TAGGACTCTA TAAATAGAGG CATGTTCCTT CTAACTTAAT     240

TAGCATTCAC AATGTAGTTT TAAGGGCTTT GAGAGTTTTG GTTAGAGGGA GAATTTGTGA     300

ACCTCTCATG TATTCCGAGT GAATTGGTTG AGGTTGTTTC CCTCTGTATT TTGTACTCTC     360
```

-continued

```
ATGTTTATAG TGGATTGCTC ATTTCCTTTG TGGACGTAGG TCGATTGACC GAACCACGTT    420

AAATTTTTGT GTCTTTTGGT ATATTTCCTG TTCTTCTTAC TCGTGGTCTT TCGAGGTTTG    480

CTTTGCTAGC TTCCGCGTTT ACACCTGCTT ATTTTCGGTC CTAACAAGTG GTATCAGAGC    540

CAGATTCAAT AATGGAGTCA GGTGTAGTGG TTCGATAATC GATGATTGAA CCAAGTTAGA    600

AAGAGGTGTT CATCTTGACG GGTGTAGTTC TAGCCGCAAC CTTTTTGACA GTAATGAAGA    660

TTTTGATGGA GAAATTGTTT CAGAGAGGTT CTCTGTGTTG AGACATAAAT TTTGTAAAGG    720

AGATTATGGA GAGGAGAAGC AAGTTGTTGA AGATTAAGTA AAGAAGGTGG ACAAATCTAT    780

TTTGTCAGAA ATTCAGGCCA AGGGGAGAT TTGTTGGGTT TTATTTGCCC TGATTTTTA     840

CCATAAATAG GTTTTCCTTT AAGGAAAAGG TTTTGAATTG ACTATTCTTT TTTTGGTAGG    900

AAAAGGTTTA GGATTCTATA AATAGAGGCA TGTTCCTTCT AACTTAATTA GCATTCACAA    960

TGTAGTTTTA AGGGCTTTGA GAGTTTTGGT TAGAGGGAGA ATTTGTGAAC CTCTCATGTA   1020

TTCCGAGTGA ATTGGTTGAG GTTGTTTCCC TCTGTATTTT GTACTCTCAT GTTTATAGTG   1080

GATTGCTCAT TTCCTTTGTG GACGTAGGTC GATTGACCGA ACCACGTTAA ATCTTTGTGT   1140

CTTTTGGTAT ATTTCTCGTT GTCTTCTTAC TCGTGGTCTT TCGAGGTTTG CTTTGCTAGC   1200

TTCCGCGTTT ACACCTGCTT ATTTGCGGTC CTAACAGAGT TCGATGGGTT GAATCTATAA   1260

AAAGAAAAAT ATACTCGTGA TTCACGATTA TTTATATGAA AATATAATAA ATATTGAATT   1320

TCCTTTGCTA TTTCTTATGT TTACGTCTTT ATATTTCAAA TTATTCCACC AATACTGACA   1380

AGCCCTAGGC CATCTCTAGG AAATTCATAC AATTTTTTTT TTGTTGTTAA CTAGTTAAAT   1440

TGGCAGCCTT AAAGATTATT GTAAAATTCA AGGCAACTTC CTCAAGTACT ACAACTACAT   1500

TGTAACATCC CAGTCAAAGT GTCCTAAAAT TTTATAAAAT TTGACACATG AAACAATAGC   1560

ACAATAAATT TTAGTACTAT TGCAGCCATG GCCCATAAGC CATCATGTAT TATAGTCAAA   1620

ATGGGTCCTT TTCCAATTTG TCTTGATCCC AAAATCCCTT TGTAGGTAAG ATGGTTCAAC   1680

AAGGAACTAT GACTCTTAAG GTAGACTTGG ACTCATAGAC TTGTCATAAC TCATAAAGAC   1740

TTGGAATATA ATAATTATTC ATTTAAATTA TAATTCTCTA CTTTAATATC TTCTACTATA   1800

AATACCCTTT CAAAGCCTCA TTATTTGTAC ATCAAACATT GATATTCATC TCTTCAATCT   1860

TTTGTATTCA CATATTCTAT TTATTCAATA CACTTAGGAA AACACTTTAC CAAGAAATTA   1920

AGATG                                                              1925
```

(2) INFORMATION FOR SEQ ID NO: 2:

(i) SEQUENCE CHARACTERISTICS:
        (A) LENGTH: 2510 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: ACO2 PROMOTER (xi) SEQUENCE DESCRIPTION: SEQ ID NO: 2:

```
GAATTCAGAA TTTTATTTTT TTATCTCCTG ATCGAATCTG TTTACACTAA AATTACTCGT     60

TAATAGTTGA TTAAATTGGA TAAATTCATA CTTGAAAATA AAAGGTTTCG GTGATGGAGG    120

GAAATGACAG ATCTAAAAGT TTGTTTACTA GTTAACGTGA AACCAGTAAT TTTTGTTTGG    180

ATCTTAGATC TATTAAATAG TTACACACAT TTTAATATTA ACCATATTGT GGTACTAATG    240

TCGTTCTAGA TTAATACGTA ATCGAGTATT GTCTAATCTC CCTTGTTACT AATTACTCGC    300
```

-continued

```
ATACGTTTAC TTCCACTTAT GTATCTTATG TATTTTATTG CTACATACTA TTTTCTTCTC        360

TTCATTATAT CCAGCATGAC TGATTTACTA TTATATTTTT CTATTTACTA TTATATTTTT        420

CTTTCTCATA CTTGATTTTA TTAATGATTT ACTATGATCT ATCAATAACA ACTTATTTAC        480

CTTCAAAAGA TATAATCAAG ACTGTGTACA TATCAATCAC TTGATATATT TTTACTCGTT        540

AATATTATTT TTTTAATCAT CGCAACTAAC ATACTTATTG ACTAATAAAA TATAAATGAC        600

TTTTCACACT TGTTTGAAGC CATATAAGTT TTTCTTCGAT CTACATCGAT ATAAGTTCTT        660

GGTCAAAGAT TGCATATTCT GGATATATGC TTTGTAATTA AGAAAAAAAA GGGAATTAGT        720

TAAGATAAAT TTCTACAATT ATTATACAAA AGTTAGGTTA GGTTGATGAA AAAGTGTATG        780

ACAAAGCAAA AATAAAAAAT AAAACTATGA TATGTTCAAA ATTCAAATAT TTAGTCAAGA        840

ATAGTTACTT AGAATTTAAT TGGATTAAAT GAAATAATTA AAAAACTCGT GGTTCTTATG        900

TCTAACAAAA AAATCATGTT GCCAACTTAT ATTTAATGTA TTGCCTAACA AAAGTAATTC        960

GGGCCGAACG GACAAGATCT TAATTAAATT GACTTTTTAA AAATTTGAAA CACGCACAAA       1020

ATTAATGTTT TTTTCGATCA AAAAGTAAAA ATACTAATTC TATATCAACC GTTCACTATA       1080

AAATTCCACT AACAATCAAC TTTTTTGTTT TGAAATCAAT TTTGTTTATC ATTCTATTTC       1140

ATATTTTTTT TAAAATAACA ATATTTTTAT TAATAATAGT TAAATAATAT TCAAACAAAC       1200

GTTATCGTTA CAGGGTTTTT GACTATATTA AGAAACTTC CATGGAGCAA ATGTGCAGCC       1260

CTAAAAATGT GAATTGTGTG TTAACTTCTA AATAGTATCC TTTTGTCAAA TTGAACCAAA       1320

CATTTTATAA TGACACATGA AAAAAAAAAA TTAAACAAAA AAATTTAGTC AAATTGATCA       1380

AAATTTAACC ACTAGAAAAT GGGTCCAAAT TCTAATTGTC CCAACTCTAA TGGGGTAGAT       1440

CAGAAGGCTA TTGGAAGATT ACTAGGTATA TGTCACTTTC GATCGGTATA AATATTGAAT       1500

AATTTTATCG ATTTAGCATT TAAATAAGAG CAAAAATAAA GTGTTTGGCA GAATTCGATG       1560

GCCTAATTTA AATTTTATAT TTATCTTAAA AAGCTCATCG AACGTATTTT AAAAACTAAA       1620

TAATTTAATA AACTAAGATA TTTCCCTTAG TTAGAAGGAT TGAGCAAAAG GTATGATTGT       1680

GGGTCAGATC AATCCATTCC GTTCTTCAGG GAAGATCTAT GGAATAGGAA AGCCAAAACG       1740

GATCTATCAA AACAGATCTA TTCTAAGTAA ATACTTGGTC GATACGAGAC TCTTTCTTAG       1800

TTCAGTGGTG TTTGAAAGCA GTCTACAACG AATCAAGCAG GTCCAGTAAC AACGGATAAC       1860

GGTCCTCACC GCGTTACCGA GGACCTCGTT TCAAAAAAAT ACGACGCCTG GGGGCTTTAC       1920

CAGGACTAAC TAATAAAAAG CCTAGGACCG GAAGTGATCT TAGAAACCAA TCGCGTTTCG       1980

GTAAAAAACC TCAATATCGT ATTCGGATAC ATTTTCATCT TAAAAATATA ATTTTTCGAC       2040

GAACATAATT CAATTGAACC ACATGTATCT AGCTTCCTCT TTAAGCTTAA GCAGATGAAA       2100

CAAGAACTTA AAAAAATAAT TATGTAATTT TCGTTATCTA TATTAAAGTT AAACTAAACA       2160

TAAATTTACC CAAAAAAAAA TTTATAATAA ATATAAAGTA ATCCCCTATA AAGTGATTAC       2220

ATATTGAGAA CCCAAAATTA TTATATTTCT ACTGAAATTT AACTTTTATT AGTTAATCCA       2280

TTGGCCACAA CCTAGTGTGG AATACCACTA TTCAATTATT ATATATTCCC TACTAGCTAT       2340

ATATGATTTA TTTCCCTATA AATACCCAAA CAAAGCCTCA ATCTTTTACA CACACACCAA       2400

AAAAAGAAAA CTCACTTTCA ATATCTTCCA TCTTTTTATT CCACACACTA TTTACTCTAA       2460

AAAAGAAAAA AAAAACATTT TCTTCTATTT CTTCAAGAAA TTAAAAAATG                  2510
```

(2) INFORMATION FOR SEQ ID NO: 3:

(i) SEQUENCE CHARACTERISTICS:

(A) LENGTH: 2483 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: ACO3 PROMOTER (xi) SEQUENCE DESCRIPTION: SEQ ID NO: 3:

| | | | | | |
|---|---|---|---|---|---|
| GTCGACCTGC | GGATCAACGG | ATCAAATTAA | TTTGATATTT | TAAATTAAAA | TTTTGAATAT | 60 |
| TAAAAAACTA | TACGAAAAGT | ACTATACTGT | AATTTTTTTT | TACAGATTAA | TATGATGAAA | 120 |
| AGATACATAG | TAAAATATTA | GTCAAAGTTC | TTATAGTTTG | ACTCTAAAAA | AAGAAAATCG | 180 |
| TGATAATTAA | AAGTTGACGA | AGGGAATAAT | TAGTTTGTTC | TAGCCTGCAT | ATTTCATCAG | 240 |
| CTTAGATTTT | ATTAGCTGTA | CGAAATTCAA | CGATTAGTTA | ATTAGGTAAA | GTTGTTGATT | 300 |
| AACAATTAAA | TGGAATGACA | TAGCTAAAGT | AACAAAAATA | TAAAATATGA | TACGTCGAAA | 360 |
| ATTCAAACGT | CCTAGTCAAA | GATAATTAAT | TAAGCCTAGA | TTTGGCTTAA | GAATATAATA | 420 |
| ACTAGAACTC | GTGATTGCAG | ACTCTATAAT | TACCTCAAAT | TCATTGTTAA | TTTTTTAAAA | 480 |
| TGTCAAATGC | ATTTCCAATG | ATCACATGGC | CGCCCTCAAA | GAAATGACT | TCAATAACAA | 540 |
| AAAATAACAT | TAATAGTAAA | TAAATTAATG | AATTGTTATT | TTAAAAAATC | AATTAAGAGT | 600 |
| GGTTAGCGTA | ATATACTAGG | AAATTTTATA | TGAATCTCAT | AGTGTTAAAA | GTTAATTACA | 660 |
| TCATATTTTT | ATTCTTTTTT | AAATTTCAAA | AATTCTTTAA | ATTTTGTGGA | ATTCGAATAT | 720 |
| ATTCCAAAAC | ATTTAGATAC | ATCGCGTCCA | ATTTCAGATA | TATTGTTCAA | CCTTTTGATA | 780 |
| CATCACATTT | TCATTTTAGA | CACAACACTC | AACCGGTTCA | TTTTAGATAC | ATCACTCAGC | 840 |
| GTCCGGATAC | ATCGCGTTTA | GAAATGTATC | CGGCTGAATC | AACGCATAAA | GTGATGTATT | 900 |
| ACGTCCCGAT | ACATCGCGTA | TAGTGATGAG | TCAGACCGTA | TCCAATTGAT | ATATCGCATA | 960 |
| AACTGATGTA | TTACGTCCTG | ATATATACAT | CATGTAAAAG | GTGATGTATT | CATGAATACG | 1020 |
| AGAGATTAGG | GTATGTGTAA | CTTTTTCAAG | TTATAAATTT | TTTTTAGAGA | ATATGATAAA | 1080 |
| ATAAAATTAA | TGTAATTTAA | TTGGTTAATT | TTTCCGGATT | TGATTAAAA | AAAAAATACA | 1140 |
| AGAGAGAGTA | TAGTGATGAA | GCGGAATCTT | AGGGAAGATT | TCTAAAATTA | TGTCTCTTTT | 1200 |
| TTTATGATTG | TAATATCGAG | TAGCTCACAA | GCCTCAATTG | CAACTTCATC | AGTATTTGTT | 1260 |
| ATCTCCTATC | ATGTACTAAG | TACTAAGTAA | CGTTTCTCAT | TTAGAGTTAG | AAAAATAAAA | 1320 |
| AGCAATCACC | TAGTGTTTCC | GTTCAATTAA | AAGATAGCTT | CTACGGCCGT | ATGTTTTAGC | 1380 |
| AAAACTTTTA | GTTTCATTAA | CTCGGGAAAA | ATTTAGAAGA | CATGGAAGTT | CTGCACTAAA | 1440 |
| TTGCACTACA | ATTTGTGTAA | CAAGAAAAAA | TTAATCAAGT | CAACGGATAG | AAATTTCATA | 1500 |
| TGAAAGATAT | ATGGGGAGCG | TTAAGATAGA | TTCGACTGAA | CTCAATAATT | TTAGTTCAAA | 1560 |
| TCATGCATTT | TATTTTAGAA | TTTTATTTGA | ATACATACAA | ATAATTAATT | CAGAACCAGT | 1620 |
| AATCTAAAAA | GATGAGAACC | GAGACTCAAT | AAGGTTCAAG | TCTTAGCTTG | GCGCCTATCG | 1680 |
| TGCAATGTGC | TAAGTACAAT | CATGCACTTG | ATTGAATTTA | CTTAGAAAAT | TAGGGAACGA | 1740 |
| TTTCTCACTT | AAAATACATT | TTTTCCTTCT | TTTCTTTGAT | GATGCACTCA | TATTCTAAAA | 1800 |
| ATTTTAGATT | CAGTCACGTC | CGACATTAAA | AACTTTCAAG | TGTGAGGCAA | CTTGGTCCGA | 1860 |
| CTCTGAACCA | AGAAATTTAT | AATAACAGAT | GAAACAATAT | CATCAAATTA | GCTTTCACTA | 1920 |
| GAGCAGCCTC | TTCAGACAAA | GCCCTTTTTA | TATTAAATAT | ATATATACAG | GTCAAGATAA | 1980 |
| AAGGGAAAAT | CATTTTTAGC | CACCAAAAAA | TTGGTCATTT | TCCAATAGTA | CATCTTTAAT | 2040 |

TAGCTCCAAA ATTAATCCCA CTTGTGTTAG GGTAAGAAGT GTCCAATAAG TAACTGTGAC    2100

CAGAATTCTA TAGCACCAGC TACACTTATG CTCCGGCTCG TATGTGTGGA TGTGAGCGGA    2160

TACATTCACA CAGGAACAGC TATGACATGA TACGAATTAA TACGACTCAC TATAGGAATC    2220

TGTAAGTGGA CTTGACTTTG GGGGTTTGGG ACTTGGGTGG GGCATTGTGA GACTTGGAAT    2280

AATGTAAAGA ATTGTAGGAC CAAAAATAAG GTAATTAAAT AGCAAAATCC CACTAGTTAT    2340

ATAATTCCTA AATTCTTGAT TTCTTCTCCT ATAAATACCC TTTCAAAGAA TCACTCTTTT    2400

CTCATCAAAC ATTTTAATAT TCATCTCTTC AATCTCTTGT ATAATTCACA TCATATAATT    2460

TAATTACCAA GAAAAATTAG ATG                                            2483

(2) INFORMATION FOR SEQ ID NO: 4:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: TCA MOTIF (xi) SEQUENCE DESCRIPTION: SEQ ID NO: 4:

TCATCTTCTT                                                              10

(2) INFORMATION FOR SEQ ID NO: 5:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: GCCGCC MOTIF (xi) SEQUENCE DESCRIPTION: SEQ ID NO: 5:

TAAGAGCCGC C                                                            11

(2) INFORMATION FOR SEQ ID NO: 6:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: H-BOX (xi) SEQUENCE DESCRIPTION: SEQ ID NO: 6:

CCTACCNNNN NNNCT                                                        15

(2) INFORMATION FOR SEQ ID NO: 7:

(i) SEQUENCE CHARACTERISTICS:
        (A) LENGTH: 15 base pairs
        (B) TYPE: nucleic acid
        (C) STRANDEDNESS: single
        (D) TOPOLOGY: linear

```
    (ii) MOLECULE TYPE: DNA (genomic)

(vi) ORIGINAL SOURCE:
         (A) ORGANISM: H-BOX (xi) SEQUENCE DESCRIPTION: SEQ ID NO: 7:

CATACCNNNN NNNCT                                                    15
```

DNA CONSTRUCTS AND PLANTS INCORPORATING THEM

The present invention relates to DNA constructs and plants incorporating them. In particular, it relates to promoter sequences for the expression of genes in plants.

Gene expression is controlled by various regulatory components, including nucleic acid and protein elements. In particular, gene expression is controlled by a region commonly referred to as the "promoter" which lies upstream (5') of the protein encoding region. A promoter may be constitutive or tissue-specific, developmentally-regulated and/or inducible.

Within the promoter region there are several domains which are necessary for full function of the promoter. The first of these domains lies immediately upstream of the structural gene and forms the "core promoter region" containing consensus sequences, normally 70 base pairs immediately upstream of the gene. The core promoter region contains the characteristic CAAT and TATA boxes plus surrounding sequences, and represents a transcription initiation sequence which defines the transcription start point for the structural gene. The precise length of the core promoter region is indefinite but it is usually well-recognisable. Such a region is normally present, with some variation, in all promoters. The base sequences lying between the various well-characterised "boxes" appear to be of lesser importance.

The presence of the core promoter region defines a sequence as being a promoter: if the region is absent, the promoter is non-functional. Furthermore, the core promoter region is insufficient to provide full promoter activity. A series of regulatory sequences upstream of the core constitute the remainder of the promoter. The regulatory sequences determine expression level, the spatial and temporal pattern of expression and, for an important subset of promoters, expression under inductive conditions (regulation by external factors such as light, temperature, chemicals, hormones).

Manipulation of crop plants to alter and/or improve phenotypic characteristics (such as productivity or quality) requires the expression of heterologous genes in plant tissues. Such genetic manipulation therefore relies on the availability of means to drive and to control gene expression as required; for example, on the availability and use of suitable promoters which are effective in plants and which regulate gene expression so as to give the desired effect(s) in the transgenic plant. It is advantageous to have the choice of a variety of different promoters so that the most suitable promoter may be selected for a particular gene, construct, cell, tissue, plant or environment.

Promoters (and other regulatory components) from bacteria, viruses, fungi and plants have been used to control gene expression in plant cells. Numerous plant transformation experiments using DNA constructs comprising various promoter sequences fused to various foreign genes (for example, bacterial marker genes) have led to the identification of useful promoter sequences. It has been demonstrated that sequences up to 500–1000 bases in most instances are sufficient to allow for the regulated expression of foreign genes. However, it has also been shown that sequences much longer than 1 kb may have useful features which permit high levels of gene expression in transgenic plants. A range of naturally-occurring promoters are known to be operative in plants and have been used to drive the expression of heterologous (both foreign and endogenous) genes in plants: for example, the constitutive 35S cauliflower mosaic virus promoter, the ripening-enhanced tomato polygalacturonase promoter (Bird et al, 1988, Plant Molecular Biology, 11:651–662), the E8 promoter (Diekman & Fischer, 1988, EMBO, 7:3315–3320) and the fruit specific 2A11 promoter (Pear et al, 1989, Plant Molecular Biology, 13:639–651) and many others.

As stated above, successful genetic manipulation relies on the availability of means to control plant gene expression as required. The scientist uses a suitable expression cassette (incorporating one or more promoters and other components) to regulate gene expression in the desired manner (for example, by enhancing or reducing expression in certain tissues or at certain developmental stages). The ability to choose a suitable promoter from a range of promoters having differing activity profiles is thus important.

One object of the present invention is to provide alternative promoters capable of driving gene expression in plants. Such promoters are suitable for incorporation into DNA constructs encoding any target gene so that the target gene is expressed when the construct is transformed into a plant. It may be particularly advantageous to provide alternative promoters which exhibit particular spatial or temporal patterns of expression, for example promoters which are active in certain cell-types and/or are particularly responsive to certain developmental events and environmental conditions. This may allow more selective control of gene expression and its effects, as the target gene is only activated where and/or when it is required.

In work leading to the present invention, we have isolated and fully sequenced three ACC oxidase gene promoters from tomato. ACC oxidase is an enzyme involved in the biosynthesis of ethylene.

Ethylene is a major plant hormone which has been shown to have a variety of effects on plant growth and development in many species. Endogenous levels of ethylene increase during several stages of development and in response to various stimuli including mechanical wounding and pathogen infection, ripening of climacteric fruits and leaf and flower senescence. The biosynthetic pathway for ethylene in plants is well-established; for example, a review of ethylene biosynthesis was published by Yang and Hoffman in 1984 (Annual Review Plant Physiology, 35:155–189). The final stages of ethylene biosynthesis proceed by the following pathway:

Methionine→

S-adenosyl-L-methionine (SAM)→

1-aminocyclopropane-1-carboxylic acid (ACC) →Ethylene.

The final step in the pathway of ethylene biosynthesis is the conversion of the cyclic amino acid 1-aminocyclopropane-1-carboxylic acid (ACC) to ethylene. This reaction is catalysed by the enzyme ACC oxidase (also know as ethylene forming enzyme or EFE) which was once thought to be constitutively expressed in most tissues. However, since the cloning of the gene the messenger RNA has been shown to be induced under a number of conditions known to result in increased ethylene production (Davies and Grierson, 1989, Planta, 179:73–80; Hamilton et al, 1990, Nature, 346:284–287).

In tomato, ACC oxidase is encoded by a multigene family comprising three members, hereinafter called the Aco1 gene, the Aco2 gene and the Aco3 gene. Bouzayen et al (1993, pp 76–81 in Cellular and molecular aspects of the plant hormone ethylene, eds. Pech et al, Kluwer Academic Publishers, NL) discuss the expression and characterisation of the ACC oxidase (EFE) multigene family in tomato plants, and FIG. 1 shows the structure and similarity of the gene family. When the open reading frame regions of the three tomato ACC oxidase (Aco) genes are aligned, the overall identity is 79.3%. The 5' or 3' un-translated regions are less homologous than the coding regions.

The coding region of the Aco1 tomato gene corresponds to the TOM13 cDNA clone, first described as a ripening-related clone by Slater et al (1985, Plant Molecular Biology, 5:137–147).

The coding region of the Aco2 tomato gene corresponds to the gTOMA gene sequence published by Holdsworth et al in Nucleic Acids Research, 1987, 15:10600.

The Aco3 tomato gene is equivalent to the clone gTOMB, described (without sequence data) in Holdsworth et al, 1988, Plant Molecular Biology, 11:81–88. Because no expression of gTOMB (Aco3) was detected, Holdsworth et al suggested this was a pseudogene, thus suggesting that an active and useful promoter could not be isolated from this gene.

After the cloning of the first ACC oxidase cDNA clone (pTOM13), standard hybridisation procedures were used to isolate clones for ACC oxidase from other plant species. ACC oxidase cDNA or genomic clones have now been isolated from at least nine other species:

(1) Melon (*Cucumis melo*)
   Balague et al, 1993, Eur J Biochem, 212:27–34;
(2) Petunia (*Petunia hybrida*)
   Wang and Woodson, 1992, Plant Physiol, 100:535–536;
(3) Apple (*Malus domestica*)
   Ross et al, 1992, Plant Molecular Biology, 19:231–238;
(4) Mustard (*Brassica juncea*)
   Pua et al, 1992, Plant Molecular Biology, 19;541–544;
(5) Avocado (*Persea americana*)
   Christofferson et al, 1993, Cellular and molecular aspects of the plant hormone ethylene, Pech J C et al (eds), Kluwer, pages 65–71;
(6) Peach (*Prunus persica*)
   Callahan et al, 1992, Plant Physiol, 100:482–488;
(7) Orchid (Phalaenopsis)
   Nadeau et al, 1993, Plant Physiol, 103:31–39;
(8) Kiwifruit (*Actinidia deliciosa*)
   Macdiarmid and Gardiner, 1993, Plant Physiol, 101:691–692;
(9) Carnation (*Dianthus caryophyllus*)
   Wang et al, 1991, Plant Physiol, 96:1000–1001.

The whole or part of the protein coding regions of ACC oxidase genes may be incorporated into DNA constructs for plant transformation. International patent application publication number WO91/01375 describes a method of modifying ethylene biosynthesis in plants by using DNA constructs based on genes encoding an enzyme involved in ethylene biosynthesis (such as ACC oxidase). Sense constructs as well as antisense constructs may be used to regulate gene/enzyme activity.

We have now isolated and fully sequenced three ACC oxidase gene promoters from tomato, and have characterised the activity and expression patterns of these promoters. Such promoters may be used to drive the expression of target genes encoded by DNA constructs within transgenic plants.

According to the present invention, there is provided a DNA sequence encoding a gene promoter capable of driving gene expression in plants which is selected from the group consisting of the Aco1 gene promoter having the sequence shown as SEQ ID NO: 1 or active variants thereof, the Aco2 gene promoter having the sequence shown as SEQ ID NO: 2 or active variants thereof, and the Aco3 gene promoter having the sequence shown as SEQ ID NO: 3 or active variants thereof. "Active variants" are DNA sequences homologous to SEQ ID NO: 1, SEQ ID NO: 2 or SEQ ID NO: 3 which retain promoter activity.

The nucleotide sequence of the Aco1 promoter is shown as SEQ ID NO: 1 (1925 bases). The ATG start codon is shown at the end of the promoter sequence (base number 1923 to 1925). The putative TATA-box is between base number 1797 and base number 1802. The transcriptional start site is at base number 1826 (for the Aco1 gene promoter, the naturally-occurring downstream coding sequence is TOM13). The Aco1 promoter was isolated by inverse PCR as it could not be cloned by conventional procedures.

The nucleotide sequence of the Aco2 promoter is shown as SEQ ID NO: 2 (2510 bases). The ATG start codon is shown at the end of the promoter sequence (base number 2508 to 2510). The putative TATA-box is between base number 2357 and base number 2362. The transcriptional start site is at base number 2386. The genomic clone for Aco2 was isolated from a tomato genomic DNA library using the TOM13 cDNA clone as a probe. The Aco2 (gTOMA) gene sequence published by Holdsworth et al, 1987 (Nucleic Acids Research, 15:10600) included a very limited promoter region (approximately 350 base pairs) starting at base number 2083 in SEQ ID NO: 2. We now provide over 2 kb of additional sequence derived from two EcoRI fragments (1.3 kb and 1.6 kb) of the same λ-clone.

The nucleotide sequence of the Aco3 promoter is shown as SEQ ID NO: 3 (2483 bases). The ATG start codon is shown at the end of the promoter sequence (base number 2481 to 2483). The putative TATA-box is between base number 2370 and base number 2375. The transcriptional start site is at base number 2404. The genomic clone for Aco3 was isolated from a tomato genomic DNA library using the TOM13 cDNA clone as a probe. We have shown that the Aco3 (gTOMB) gene is not a pseudogene as had been suggested in Holdsworth et al, 1988 (Plant Molecular Biology, 11:81–88). The Aco3 gene and promoter are contained in the 4.2 kb genomic insert of clone gTOMB. We have now sequenced the 2.4 kb upstream sequence that acts as a promoter to direct Aco3 gene expression. Having completely sequenced the Aco3 gene, we found the coding region (but not promoter) is homologous to the sequence of the cDNA clone pHTOM5 published by Spanu et al, 1991, EMBO J, 10:2007–2013 (a clone expressed in cultured cells in response to treatment with fungal elicitor).

The sequences of the Aco1, Aco2 and Aco3 gene promoters have not previously been elucidated. Example 1 gives information on the limited homology between the Aco promoters and known promoters.

The Aco promoters may be synthesised ab initio using the sequences shown in SEQ ID NO: 1, SEQ ID NO: 2 and SEQ ID NO: 3 as a guide. Alternatively, the Aco2 and Aco3 promoters may be isolated from plant genomic DNA libraries using suitable probes derived from the said sequences and the Aco1 promoter may be isolated using a PCR approach.

Active variants of the Aco promoters may also be generated. It may be possible to alter the level or type of activity of the Aco promoters by manipulating their sequences: for example, by altering the nucleotide sequence in key regulatory regions, by truncating the sequence or by deleting parts within the sequence. Segments of the Aco promoter sequences of between 100 and 2000 bases in length may be useful as plant-operative promoters.

Gene specific probes were generated from the 3' UTR region of each of the Aco1, Aco2 and Aco3 genes. These were used in conjunction with a ribonuclease protection assay (Example 2) to analyse the differential expression of the Aco genes in various tissues and in response to different stimuli known to induce ethylene biosynthesis. These experiments have indicated where and when the Aco genes are expressed (that is, where and when the Aco promoters are active). ACC oxidase gene expression is highly regulated. Different genes are expressed in various tissues in response to different stimuli and the messages accumulate to different levels. ACC oxidase genes are highly inducible and therefore not constitutively expressed. There may also be post-transcriptional regulation of the Aco genes.

The Aco1 promoter is the strongest Aco promoter, being strongly expressed during ripening and in response to wounding. It may be useful for expressing genes during ripening or in response to wounding (for example, by driving "defense" genes) or for controlling expression of antisense constructs. The Aco1 gene and its encoded product has a likely role in the senescence of leaves, flowers and fruit. The Aco1 promoter may be useful for driving expression of target genes used to modify the senescence process in plants.

The Aco2 gene is expressed in seedlings and flowers. The Aco2 promoter could have utility in specific circumstances or cell types.

The Aco3 gene is expressed during ripening and in response to wounding, although less strongly than Aco1. Aco3 may act as the trigger to induce Aco1 during autocatalytic ethylene production that occurs during fruit ripening and flower senescence.

All the Aco genes appear to play a role in postpollination events in tomato flowers and may also be important for root development during germination.

In practice the promoter of the invention may be inserted as a promoter sequence in a recombinant gene construct destined for use in a plant. The construct is then inserted into the plant by transformation. Any plant species may be transformed with the construct, and any suitable transformation method may be employed.

According to a second aspect of the invention, there is provided a plant gene expression cassette comprising a promoter operatively linked to a target gene, the promoter being selected from the group consisting of the Aco1 gene promoter having the sequence shown as SEQ ID NO: 1 or active variants thereof, the Aco2 gene promoter having the sequence shown as SEQ ID NO: 2 or active variants thereof, and the Aco3 gene promoter having the sequence shown as SEQ ID NO: 3 or active variants thereof.

The target gene is a DNA sequence which may be derived from an endogenous plant gene or from a foreign gene of plant, fungal, algal, bacterial, viral or animal origin. Normally it is a sequence other than the sequence encoding the ACC oxidase protein which follows the Aco promoter in the naturally-occuring Aco gene. The target gene may be a single gene or a series of genes. The target gene is adapted to be transcribed into functional RNA under the action of plant cell enzymes such as RNA polymerase. Functional RNA is RNA which affects the biochemistry of the cell: for example, it may be mRNA which is translated into protein by ribosomes or it may be RNA which inhibits the translation of mRNA related to it. Thus the target gene sequence may be a sense sequence encoding at least part of a functional protein or an antisense sequence.

The expression cassette is suitable for general use in plants. In practice the DNA construct comprising the expression cassette of the invention is inserted into a plant by transformation. Any transformation method suitable for the target plant or plant cells may be employed, including infection by *Agrobacterium tumefaciens* containing recombinant Ti plasmids, electroporation, microinjection of cells and protoplasts, microprojectile transformation, pollen tube transformation and transformation of plant cells using mineral fibres (U.S. Pat. No. 5,302,523, International Patent Application Publication Number WO94/28148). The transformed cells may then in suitable cases be regenerated into whole plants in which the new nuclear material is stably incorporated into the genome. Both transformed monocotyledonous and dicotyledonous plants may be obtained in this way. Transgenic plant technology is for example described in the following publications: Swain W F, 1991, TIBTECH 9: 107–109; Ma J K C et al, 1994, Eur J Immunology 24: 131–138; Hiatt A et al, 1992, FEBS Letters 307:71–75; Hein M B et al, 1991, Biotechnology Progress 7: 455–461; Duering K, 1990, Plant Molecular Biology 15: 281–294.

Examples of genetically modified plants which may be produced include but are not limited to field crops, cereals, fruit and vegetables such as: canola, sunflower, tobacco, sugarbeet, cotton, soya, maize, wheat, barley, rice, sorghum, tomatoes, mangoes, peaches, apples, pears, strawberries, bananas, melons, potatoes, carrot, lettuce, cabbage, onion.

The invention further provides a plant cell containing a gene expression cassette according to the invention. The gene expression cassette may be stably incorporated in the plant's genome by transformation. The invention also provides a plant tissue or a plant comprising such cells, and plants or seeds derived therefrom.

The invention further provides a method for controlling plant gene expression comprising transforming a plant cell with a plant gene expression cassette having an Aco promoter operatively linked to a target gene, whereby the activated promoter drives expression of the target gene. The promoter may be activated under certain spatial, temporal, developmental and/or environmental conditions.

In order to determine their temporal and spatial expression, the promoter fragments of the Aco genes are fused to the GUS (β-glucuronidase) reporter gene in DNA constructs suitable for plant transformation. GUS accumulation in transgenic plants may then be monitored. Example 3 describes some of these experiments. Transgenic plants expressing a GUS reporter gene under control of the Aco1 promoter have been generated. Analysis has shown that GUS is expressed in wounded tissue (such as leaves) and ripening fruit (Example 3). Transgenic plants expressing a GUS reporter gene under control of the Aco2 promoter or the Aco3 promoter may also be generated for analysis.

The invention will now be described by way of example only with reference to the accompanying drawings in which.

Figure 1:
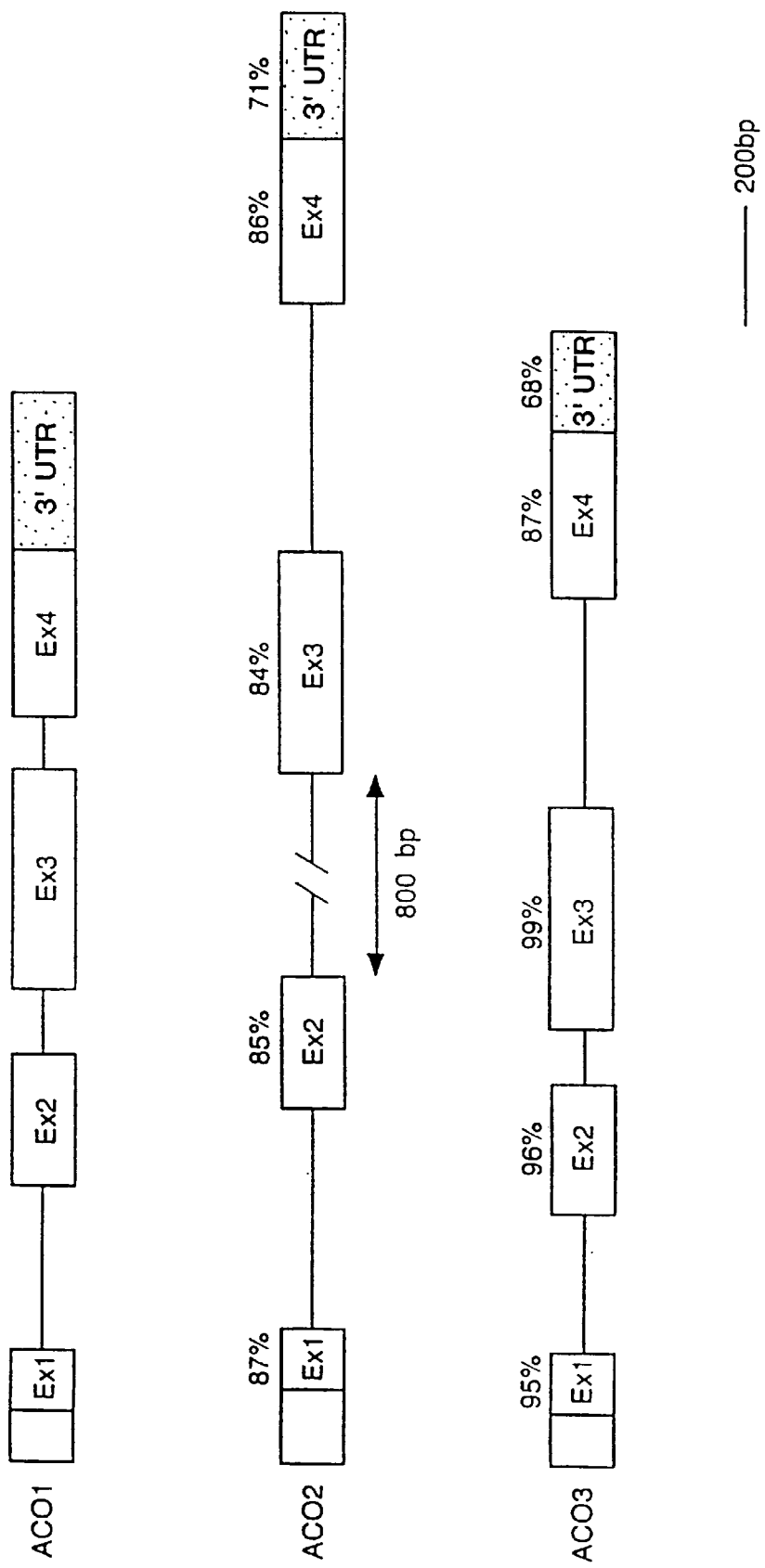
FIG. 1 is a diagram showing the structure and similarity of the tomato ACC oxidase gene family.

The invention is also described with reference to the SEQUENCE LISTING in which:

SEQ ID NO: 1 shows the nucleotide sequence of the Aco1 promoter;

SEQ ID NO: 2 shows the nucleotide sequence of the Aco2 promoter;

SEQ ID NO: 3 shows the nucleotide sequence of the Aco3 promoter;

SEQ ID NO: 4 shows the nucleotide sequence of the TCA-motif;

SEQ ID NO: 5 shows the nucleotide sequence of the GCCGCC-motif tobacco

SEQ ID NO: 6 shows the nucleotide sequence of the H-box from a range of inducible promoters;

SEQ ID NO: 7 shows the nucleotide sequence of the H-box from the Aco3 promoter.

EXAMPLE 1

Analysis of the Aco1, Aco2 and Aco3 Gene Promoter Sequences (a) Homology searches Homology searches with the EMBL database using the BLASTN and BESTFIT algorithms for the promoters of the tomato Aco1, Aco2 and Aco3 genes gave the following results.

Aco1 promoter tomato 2A11 gene (Van Haren and Houck, 1991, PMB, 17:615–630):
87% identity in 511 bp overlap tomato E4 gene (Cordes et al, 1989, Plant Cell, 1:1025–1034):
84.5% identity in 413 bp overlap petunia (Ph) ACC oxidase genes
(Tang et al, 1993, PMB, 23:1151–1164):
Ph-Aco1:
70% identity in 249 bp overlap
nt −728 to −563 (Ph-Aco1)
nt −369 to −134 (Le-Aco1)
Ph-Aco3:
74% identity in 330 bp overlap comprising the region at and before the TATA-box
Ph-Aco4:
57% identity in 118 bp overlap comprising TATA-box and 5'UTR in both genes
Aco2 promoter
petunia ACC oxidase genes:
homologies in 5'UTR and around TATA-boxes with all 3 genes
β-1,3 glucanase genes
(Linthorst et al, 1990, PNAS, 87:8756–8760) and chitinase genes
(Broglie et al, 1989, Plant Cell, 1:599–607) from tobacco and broad bean: short stretches (60–70% identity in 70–100 bp overlaps)
Aco3 promoter:
potato WTN2 gene
(Stanford et al, 1989, MGG, 215:200–208):
85% identity in 157 bp overlap
nt −2384 to −2226 (Aco3)
nt −289 to −132 (WIN2)
petunia ACC oxidase genes:
Ph-Aco1:
68% identity in 57 bp overlap
nt −434 to −378 (Le-Aco3)
nt −682 to −626 (Ph-Aco1)
Ph-Aco3:
86% identity in 38 bp overlap around TATA-box
Ph-Aco4:
74% identity in 54 bp overlap
nt −534 to −480 (Le-Aco3)
nt −417 to −367 (Ph-Aco4)
poplar proteinase inhibitor gene
(Bradshaw et al, 1990, PMB, 14:51–59):
70% identity in 57 bp overlap
tobacco PR1 gene
(Oshima et al, 1987, FEBS Lett, 225:243–246):
62% identity in 80 bp overlap around TATA-box
(b) Occurrence of cis-acting elements The sequences of the tomato Aco gene promoters were searched for certain cis-acting elements (boxes) known from ethylene/wound/elicitor responsive genes.

The TCA-motif "TCATCTTCTT" (SEQ ID NO: 4) is a 10 bp motif which occurs in over thirty stress and pathogen inducible promoters (Goldsborough et al, 1993, Plant J, 3:563–571) and is bound by tobacco nuclear proteins. It occurs seven times in the tomato Aco1 gene promoter (2 mismatches), five times in Aco2 (1 and 2 mismatches) and eight times in Aco3 (1 and 2 mismatches).

The GCCGCC-motif is found in several ethylene induced PR genes from tobacco which contain a highly conserved 11 bp element "TAAGAGCCGCC" (SEQ ID NO: 5). Part of this is present in a bean chitinase minimal ethylene response element. It is presumed not to occur in ripening/senescence related ethylene responsive genes (Eyal et al, 1993, Plant J, 4:225–234; Meller et al, 1993, PMB, 23:453–463; Hart et al, 1993, PMB, 21:121–131). It is found in Aco3 at nucleotide (nt) −1895, and in Aco1 and Aco2 only with 1 mismatch.

There is an 8 bp element in the carnation GST1 promoter ("ATTTCAAA") (Itzhaki et al, 1994, PNAS, 91:8925–8929) and the tomato E4 promoter ("AATTCAAA") (Montgomery et al, 1993, PNAS, 90:5943) in regions necessary for ethylene response, bound by nuclear proteins from senescing petals/unripe fruit. The element occurs three times in the tomato Aco1 gene, twice in Aco2 and twice in Aco3.

The H-box "CCTACC(N)$_7$CT" (SEQ ID NO: 6) occurs in a range of inducible promoters responsive to various stimuli (ABA, light, UV irradiation, elicitors) (Dixon et al, 1988, Ann Rev Phytopathol, 32:479–502). It occurs as "CATACC(N)$_7$CT" (SEQ ID NO: 7) at nucleotide −1383 in Aco3 but not in Aco1 or Aco2.

EXAMPLE 2

Ribonuclease Protection Assays: Analysis of the Differential Regulation of the ACC Oxidase Gene Family from Tomato (a) Method To study ACC oxidase gene expression, mRNA was extracted from various tissues in ripening tomato fruit, in ethylene treated fruit, in germinating seeds and in flowers at various stages of development (stage 1, closed buds; stage 2, buds begining to open but petals green; stage 3, fully open flowers; stage 4, early senescent flowers—curled but not faded petals; stage 5, late senescent flowers—both petals and sepals curled and petals turning brown). Total RNA was extracted from plants as described in Hamilton et al, 1990, Nature, 346:284–287 and 25 μg was used routinely in each ribonuclease protection assay.

Radiolabelled ($P^{32*}$) RNA probes were generated from linearised recombinant plasmids containing the 3' UTR region of each Aco gene using T7 RNA polymerase (Promega) as outlined in the Promega protocols and applications handbook. Each probe was gene-specific so that there would be no cross-hybridisation between the Aco1, Aco2 or Aco3 probes/genes. Probes were purified by separation through denaturing 8% PAGE gels. After visualisation of the full length probe by autoradiography the band was excised from the gel and the probe eluted overnight.

The mRNA was hybridised to the probe overnight at 42° C. and subsequently digested with five units of "RNAse one" (Promega) for three hours at 25° C. (Aco1) or 30° C. (Aco2 and Aco3), essentially as described in Brewer et al, 1992, Promega Notes No. 38: 1–7. Products were separated through denaturing 5% PAGE gels and visualised by autoradiography. The gels were dried and exposed to Kodak x-omat film at −70° C. with two intensifying screens for a given period described for each gel. The signal from the gel was quantified using the Ambis Radioanalytical Scanning System.

The ribonuclease protection assay is more likely to detect low abundance message as it is possible to use more RNA that can be separated through an agarose gel and blot. In addition, the hybridisation is carried out in a small volume in solution, so that the target RNA and the probe are more concentrated. Hybridisation in solution also means that all the RNA will be available to bind with the probe. The ribonuclease digests any sequences that do not completely hybridise which gives less chance of mismatch hybridisation.

(b) Results

The data show that the Aco genes of tomato are highly inducible and exhibit differential expression in various tissues at different stages of development during tomato fruit ripening. It appears that in most tissues so far analysed at least two Aco genes are expressed (for example, poster by C S Barry et al, ISPMB conference, Amsterdam, Jun. 19–24 1994).

Aco1 appears to be the most abundantly expressed of the three genes in ripening fruit where it accumulates to high levels, probably due to the autocatalytic nature of ethylene biosynthesis in this organ. Expression shows a high induction at breaker stage and persists throughout the ripening process until 12 days post breaker and probably beyond.

Expression of Aco3 is undetectable in green fruit but is induced and peaks at the breaker stage and persists throughout ripening like Aco1 but is approximately fifty times less abundant.

All three Aco genes are expressed during flower development. Larson et al (1993, pp 112–122 in Plant signals and interactions with other organisms, eds Raskin and Schultz, Am Soc Plant Physiologists) have proposed a model for interorgan signaling in pollinated carnation flowers involving three distinct postpollination events that result in ethylene production. It is possible that in tomato such a signaling pathway occurs and that the three Aco genes play a regulatory role.

Aco1 is induced four fold at the beginning of flower senescence and is also greatly induced at the onset of leaf senescence. These observations, together with its high abundance in senescing (ripening) fruit, indicate a possible general role for Aco1 during plant ageing.

Aco2 has been detected in fully open and senescing flowers at stages 3–5 and may represent a flower specific ACC oxidase.

Aco3 appears to show the highest levels of expression throughout flower development.

Table 1 shows the relative abundance of ACC oxidase mRNA in various organs and at different stages of development. In the Table, all figures are net counts per minute (cpm); N/D means "no message detected"; UW means "unwounded"; W 2 h means "2 hours after wounding".

TABLE 1

|  | Aco1 | Aco2 | Aco3 |
| --- | --- | --- | --- |
| Seed Germination |  |  |  |
| 0 day | n/d | n/d | n/d |
| 8 days | 2 | 1 | 3 |
| Leaves |  |  |  |
| UW | 1 | n/d | n/d |
| W 2h | 11 | n/d | n/d |
| senescent | 27 | n/d | 12 |
| Flowers |  |  |  |
| Fully open | 12 | 23 | 58 |
| senescent | 51 | 25 | 96 |
| FRUIT |  |  |  |
| mature green | 2 | n/d | n/d |
| breaker + 3 | 108 | n/d | 2 |

The spatial expression of Aco genes in flowers was examined in more detail. Results show that Aco1 is predominantly expressed in style, stigma and petals at the onset of petal senescence; Aco2 is mainly expressed in anthers when the flowers open fully; Aco3 is highly expressed in stipe and stigma when the flowers open and remains active through senescence.

EXAMPLE 3

Aco Promoter/GUS Constructs for Analysis in Transgenic Plants

In order to determine their temporal and spatial expression, the promoter fragments of the Aco genes were fused to the GUS reporter gene in DNA constructs suitable for plant transformation. GUS accumulation in transgenic plants is then monitored.

In addition to the promoter-GUS fusions, the constructs contain different terminators. One carries the 3'UTR of Aco3, the other carries the 3'UTR of the polygalacturonase gene. Both constructs were assembled in pBluescript and inserted in to pBIN19 and have been transformed into Agrobacterium.

Tomato plants have been transformed with Aco promoter/GUS constructs and have been analysed. GUS analysis is carried out on vegetative tissue and on mature fruiting plant material when it becomes available.

Figure 2:
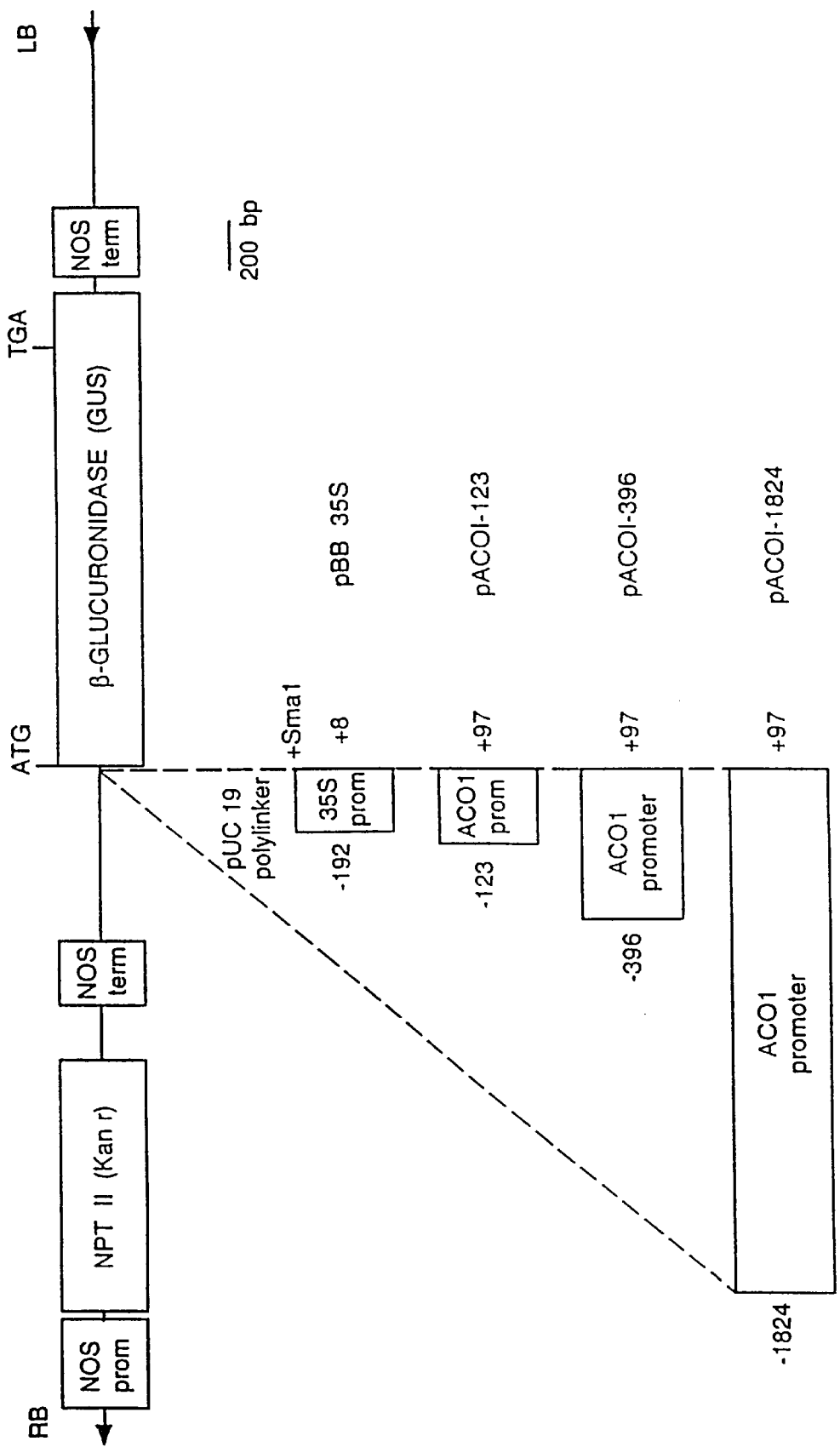
FIG. 2 is a diagram of the Aco1 promoter/GUS transformation constructs.
Figure 3:
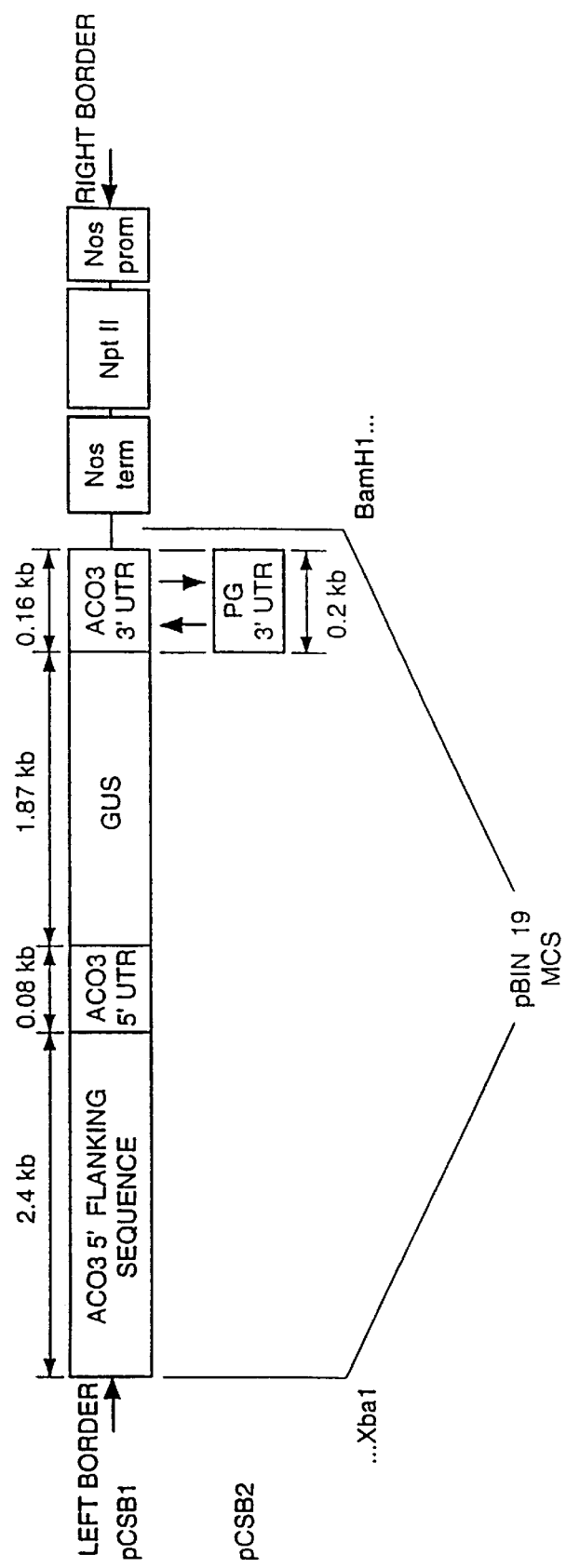
FIG. 3 is a diagram of the Aco3 promoter/GUS transformation constructs.

FIG. 2 is a diagram of the constructs which were used to transform tomato cotyledons. The Aco1 promoter region and fragments thereof plus the 5'UTR were fused to GUS using the binary vector pBIN19 with a promoterless GUS casette (pBI-101), forming the constructs pAco1-1824, pAco1-396 and pAco1-123. pACO1-123 contains the fragment of the Aco1 promoter which shows a high degree of homology within all three tomato Aco genes. The construct pBB35S was made as a control and contains 200 bp of the 35S CaMV promoter fused to GUS.

Table 2 summarises the range of GUS expression obtained with the various constructs identified in FIG. 2. The construct BB35S GUS is included for comparison: it is the GUS gene driven by the CaMV35S promoter. It also identifies, representative plants for further analysis (reported below).

TABLE 2

TOMATO TRANSFORMATION

| Construct | No. of transformants | Range of GUS activity | Representative plants (No. of T-DNA insertions) |
| --- | --- | --- | --- |
| BB35S GUS | 7 | 6: medium-high activity<br>1: no activity (rearrangement in T-DNA) | H1315 (1)<br>H1327 (2) |
| Aco1-124 | 5 | 5: GUS activity above background in ripening fruit | BB17/1 (2, one locus?)<br>H1317 (3) |
| Aco1-396 | 6 | 5: high activity<br>1: no activity (rearrangement in T-DNA) | BB13/15 (1)<br>BB4/2 (2) |
| Aco1-1825 | 8 | 2: high activity<br>2: medium-high activity, different pattern, abnormal phenotype<br>1: very low activity<br>3: no activity | BB15/1 (2, one locus?)<br>BB15/5 (1) |

Table 3 reports analysis results of a similar nature to those in Table 2 for Nicotiana transformed with the same constructs.

TABLE 3

NICOTIANA PLUMBAGINIFOLIA TRANSFORAMTION

| Construct | No. of transformants | Range of GUS activity | Representative plants (No. of T-DNA insertions) |
| --- | --- | --- | --- |
| BB35S GUS | 10 | 3: high activity<br>7: low-medium activity | Bb10/1 (1)<br>Bb10/2 (2)<br>Bb10/4 (1) |
| Aco1-124 | 9 | Most with activity above background in senescent leaves and flowers | BB9/11 (2, one locus?)<br>BB9/12 (1)<br>BB9/14 (2) |
| Aco1-396 | 19 | 14: high activity (senescent leaf) | BB8/1 (1)<br>BB8/2 (3) |

TABLE 3-continued

NICOTIANA PLUMBAGINIFOLIA TRANSFORAMTION

| Construct | No. of transformants | Range of GUS activity | Representative plants (No. of T-DNA insertions) |
|---|---|---|---|
| Aco1-1825 | 16 | 3: low-medium activity<br>2: no activity<br>10: high activity (senescent leaf)<br>2: medium activity<br>2: activity just above background<br>2: no activity | BB20/18 (1)<br><br>BB19/17 (1)<br>BB19/2 (1)<br>BB19/10 (2) |

Table 4 reports the analysis of GUS expression at various stages of plant development, showing the variation in expression levels compared with that found in young leaves.

TABLE 4

Relative levels of LEAco1 and uidA mRNA and GUS activity during plant development in two representative plants harbouring the Aco1-396 (plant BB13/15) and Aco1-1825 (plant BB15/5) constructs

| Construct | Young leaf | Expanded leaf | Senescent leaf | Petiole abscission zone | Flower stage 2 | Flower stage 4 | IM fruit | MG fruit | B + 3 fruit | B + 8 fruit |
|---|---|---|---|---|---|---|---|---|---|---|
| Aco1-396 | | | | | | | | | | |
| Aco1 mRNA[a] | 1 | 8.9 | 31.4 | nd[b] | 2.74 | 9 | 2.1 | 5.7 | 143 | 12.6 |
| GUS mRNA | 1 | 18.2 | 80 | nd | 1.5 | 2.9 | 1.25 | 9.5 | 25 | 4.8 |
| GUS activity | 1 | 109 | 1052 | 639 | 13.5 | 26.5 | 1.05 | 17.7 | 120 | 54 |
| Aco1-1825 | | | | | | | | | | |
| Aco1 mRNA | 1 | 9.2 | 39.5 | 4.47 | 3.7 | 11.1 | 0.97 | 2.6/10.8[c] | 263 | 59.5 |
| GUS mRNA | 1 | 12 | 78 | 8.5 | 2.8 | 6.7 | 3.2 | 12/54 | 45 | 8.12 |
| GUS activity | 1 | 54 | 307 | 163 | 13.6 | 22.1 | 2.6 | 20.2/51 | 101 | 78.8 |

Shown are relative levels compared to those in young leaves
[a]mRNA levels were determined fromat least two independent Northern or dot blots.
[b]nd:not determined
[c]Mature green fruit from two different stages of maturity were harvested Table 5 reports the induction of GUS expression in representative tomato plants in response to stimuli, wounding, ethylene and various infections.

TABLE 5

Fold induction of GUS activity by wounding, ethylene treatment and infection in representative tomato transformants

| | Construct | | |
|---|---|---|---|
| | Aco1-396 | Aco1-1825 | BB35S GUS |
| Wounding | | | |
| Leaves/2h | 2.8 ± 0.45 (4) | 4.93 ± 0.9 (6) | 1.13 ± 0.2 (6) |
| Fruit: IM/6h | 10 | 12.7 | |
| MG/6h | 1.9 ± 0.4 (2) | 1.8 ± 0.5 (2) | |
| 10 ppm ethylene | | | |
| leaves/6h | 4.4 ± 1.94 (3) | 4.26 ± 1.28 (3) | 0.67 ± 0.2 (2) |
| MG fruit/6h | 5 | 2.5 ± 0.6 (2) | |
| Seedlings, 8 das | | | |
| dark ± 20 μM ACC | 3.9 ± 0.7 (2) | 3.1 ± 0.09 (2) | 0.27 ± 0.08 (2) |
| dark ± 10 ppm ethylene | | 1.59 ± 0.26 (2) | |
| TMV infection | | | |
| 2 dpi | 4.9 | 3.4 | |
| 2 dpt | 9.4 | 5.2 | |
| uninoculated leaves | 1.8 | 2.1 | |
| 7 dpi | | 9.4 | |
| 11 dpi | | | |
| *Cladiosporum fulvum* infection | | | |
| 6 dpi | 1.5 | 2.4 | |
| 14 dpi | 3 | 5 | |
| Powdery mildew infection | | | |
| 1 dpi | 3.9 | 8.2 | |
| 2 dpi | 4.3 | 16.6 | |
| 6 dpi | 10 | 15.6 | |
| Methyl jasmonate | | | |
| 6h 10 μM | 3.5 | | |
| 100 μM | 6.7 | 4.5 | |
| 5 mM α-aminobutyric acid | | | |
| 6h | 5.9 ± 0.9 (2) | 4.7 ±0.99 (2) | 1.05 ±0.18 (2) |

Table 6 reports the expression of GUS in germinating tomato seeds and seedlings in light and dark.

TABLE 6

GUS activity in germinating tomato seeds and seedlings

| Germination | Construct (plant) | | |
|---|---|---|---|
| | BB35S-GUS (H1327) | Aco1-396 (BB13/15) | Aco1-1825 (BB15/5) |
| Light | | | |
| dpi: 0 | | 33.3* | |
| 2 | | 27.8 | |
| 4 | | 38.2 | |
| 8 | | 23.6 | 38.9 |
| 14 | 4248 | 58 | |
| Light + 20 μM ACC | | | 125.8 |
| 8 dpi | | | |
| Dark | | | |
| 8 dpi | | 6.4 | 29 |
| 10 dpi | 2954 | 9.6 | 49 |
| Dark + 10 ppm C$_2$H$_4$ | | | |
| 8 dpi | | | 38.5 |
| 10 dpi | | | 90.6 |
| Dark + ACC + 2 mM Ag(S$_2$O$_3$)$_2$ | | | |
| 8 dpi | | | 121 |
| 10 dpi | | | 183 |
| Dark + 2 mM Ag(S$_2$O$_3$)$_2$ 8 dpi | | | 105 |
| Light + 3 mM Ag(S$_2$O$_3$)$_2$ 8 dpi | | | 120 |

*GUS activity in pmol/min/mg protein
Seeds were germinated on 0.7% MS agar (supplemented with 3% sucrose and 50 μg/ml kanamycin), ACC and Ag(S$_2$O$_3$)$_2$ were included in the agar. Ethylene was injected daily into airtight jars (390 ml) to the final concentration of 10 ppm.

What is claimed is:

1. A DNA sequence encoding a gene promoter capable of driving gene expression in plants which is selected from the group consisting of the Aco1 gene promoter having the sequence shown as SEQ ID NO: 1, the Aco2 gene promoter having the sequence shown as SEQ ID NO: 2, and the Aco3 gene promoter having the sequence shown as SEQ ID NO: 3.

2. A gene construct comprising the Aco1, Aco2 or Aco3 promoter as claimed in claim 1.

3. A gene construct comprising the Aco1, Aco2 or Aco3 promoter as claimed in claim 1 operatively linked to a DNA specifying an RNA.

4. A gene construct as claimed in claim 3, in which the said DNA encoding RNA is a gene regulating sequence defining an RNA in antisense orientation to a target gene.

5. A method for controlling the expression of a DNA sequence in a plant, comprising providing a gene construct comprising a gene promoter as claimed in claim 1 operatively linked to a downstream DNA specifying an RNA and a downstream 3'-transcription terminating signal, inserting said construct into a plant cell by transformation and regenerating plants from the transformed cell, wherein when said gene promoter is activated, expression of said DNA occurs.

6. A method as claimed in claim 5, the said plant being a tomato plant.

7. A plant produced by the method of claim 5.

8. A plant that has been stably transformed with at least one of the sequences of claim 1.

* * * * *